United States Patent
Yates et al.

[19]

[11] Patent Number: 5,928,275
[45] Date of Patent: Jul. 27, 1999

[54] BODY WARMER BELT

[76] Inventors: James W. Yates, Rt. 1, Box 585, Wise, Va. 24293; Ronnie L. Yates, Box 3441, Wise, Va. 24293

[21] Appl. No.: 08/866,572

[22] Filed: Jun. 2, 1997

Related U.S. Application Data

[63] Continuation of application No. 08/553,931, Nov. 6, 1995, abandoned.

[51] Int. Cl.⁶ .................................................... A61F 07/00
[52] U.S. Cl. .......................... 607/112; 607/108; 607/114; 126/204
[58] Field of Search ............................ 607/108–112, 119; 126/204

[56] References Cited

U.S. PATENT DOCUMENTS

| | | |
|---|---|---|
| 1,970,081 | 8/1934 | Eisendrath . |
| 3,075,517 | 1/1963 | Morehead . |
| 3,476,102 | 11/1969 | Sarnoff . |
| 4,527,566 | 7/1985 | Abare ...................................... 607/112 |
| 4,543,671 | 10/1985 | Monk . |
| 4,586,506 | 5/1986 | Nangle . |
| 4,587,672 | 5/1986 | Madnick et al. . |
| 4,702,235 | 10/1987 | Hong ................................... 607/108 X |
| 4,895,133 | 1/1990 | Collins et al. . |
| 4,972,832 | 11/1990 | Trapini et al. . |
| 4,998,653 | 3/1991 | LaBelle . |
| 5,038,779 | 8/1991 | Berry et al. . |
| 5,074,300 | 12/1991 | Murphy . |
| 5,088,487 | 2/1992 | Turner . |
| 5,148,804 | 9/1992 | Hill et al. ................................. 607/108 |
| 5,179,942 | 1/1993 | Drulias et al. . |
| 5,215,080 | 6/1993 | Thomas et al. .......................... 607/112 |
| 5,230,333 | 7/1993 | Yates et al. . |
| 5,269,023 | 12/1993 | Ross . |
| 5,302,806 | 4/1994 | Simmons et al. ........................ 607/108 |
| 5,378,225 | 1/1995 | Chatman, Jr. et al. . |
| 5,395,399 | 3/1995 | Rosenwald .............................. 607/114 |
| 5,398,667 | 3/1995 | Witt . |
| 5,557,801 | 9/1996 | Jakus ................................... 607/108 X |
| 5,665,057 | 9/1997 | Murphy .................................. 607/108 |
| 5,697,962 | 12/1997 | Brink et al. ............................. 607/114 |

*Primary Examiner*—Robert L. Nasser
*Attorney, Agent, or Firm*—Laubscher & Laubscher

[57] ABSTRACT

A body warming belt containing a pair of pockets adapted to receive chemical or electrical heating devices at positions directly opposite the user's kidneys, respectively, thereby to warm the user. According to a modification of the invention the warming belt may have removable pockets which can be positioned at various locations on the belt in accordance with the size of the user thereby to support the heating devices directly opposite the user's kidneys, respectively.

3 Claims, 3 Drawing Sheets

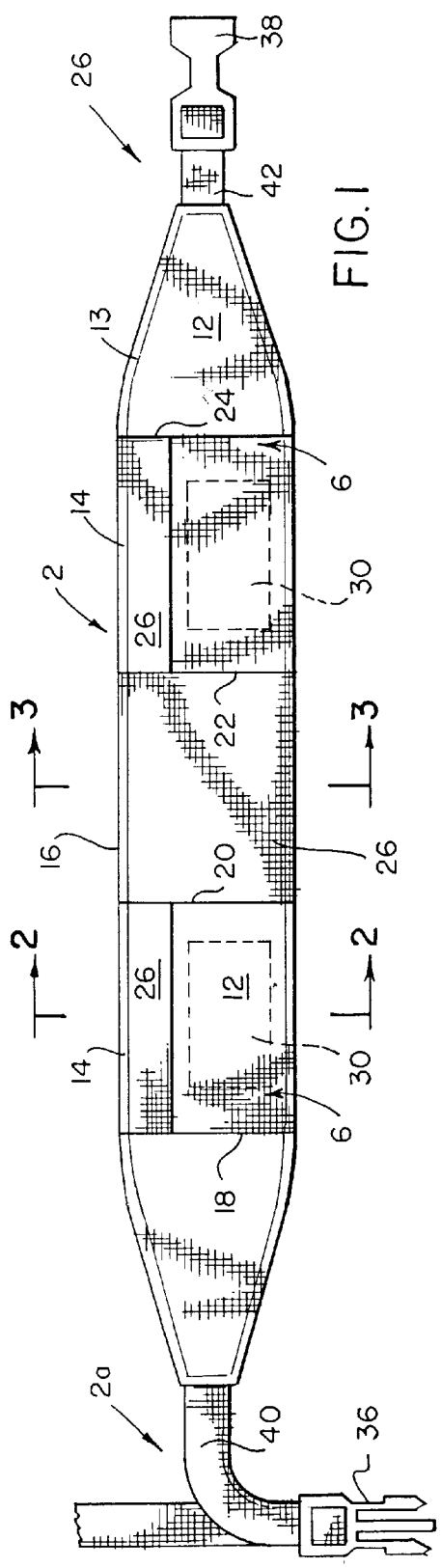
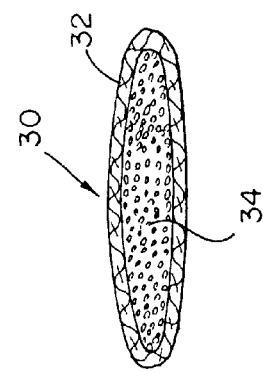
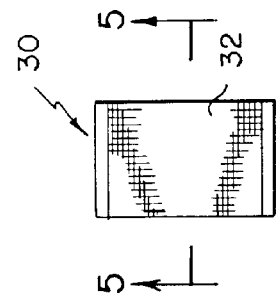
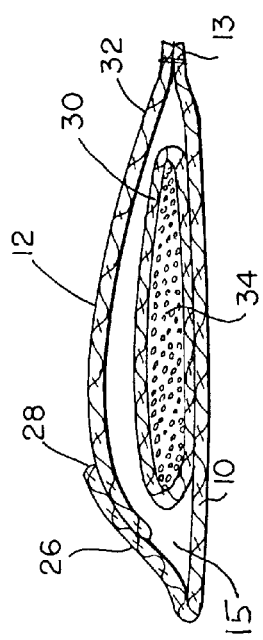
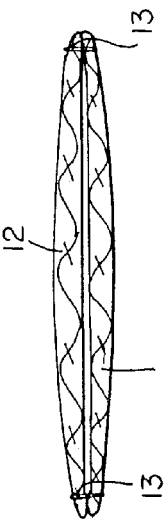

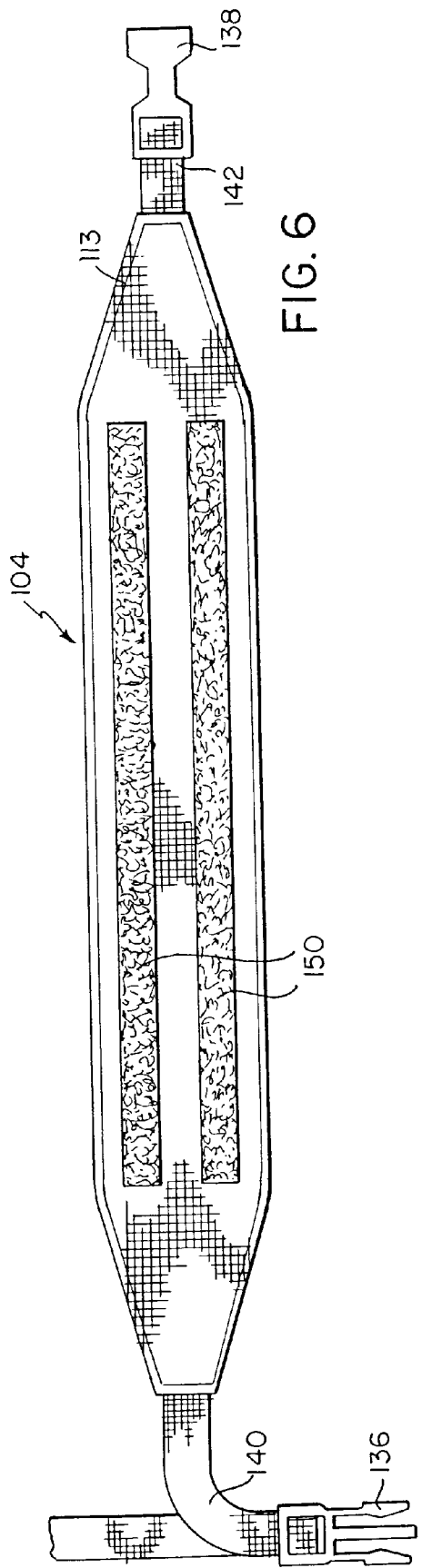
FIG. 6
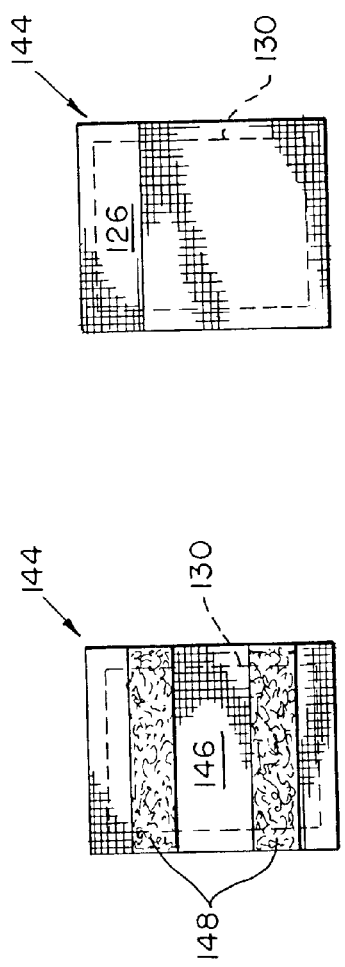
FIG. 8
FIG. 7

BODY WARMER BELT

This is a continuation of application of Ser. No. 08/553,931, filed Nov. 6, 1995, now abandoned.

STATEMENT OF THE INVENTION

The present invention relates to heated wearing apparel, and more particularly, to a heated belt for warming the kidneys of the wearer, thereby creating an overall body warming effect.

BRIEF DESCRIPTION OF THE PRIOR ART

In the human body, blood is normally warmed by the body's core which includes the vital organs (i.e. the heart, lungs, liver and kidneys). The warmed blood is then circulated, thereby warming the extremities. In fact, one method used to rewarm severely hypothermic individuals is to warm the blood through hemodialysis, thus providing internal or core rewarming. Thus, directing heat toward one or more of the vital organs is an effective and efficient method of distributing heat throughout the body.

The patented prior are contains examples of apparel designed to keep individuals, such as hunters, fishermen, spectators at stadium events, or the like warm, as well as therapeutic heating devices. For example, the Sarnoff U.S. Pat. No. 3,476,102 discloses a vest-type garment having pockets which receive thermal change heating pockets for heating or cooling the individual wearing the garment.

The Ross U.S. Pat. No. 5,269,023 discloses a body warming device which may be worn by a person to warm the hands or may be arranged to warm other portions of the body.

The Chatman, Jr. et al U.S. Pat. No. 5,378,225 discloses a heated back support for providing both heat therapy and support to user's suffering from back spasms or chronic back pain.

The Witt U.S. Pat. No. 5,398,667 discloses a cummerbund back warmer in the form of a belt which encircles the waste of the wearer.

None of these prior devices provide a simple, lightweight garment for providing a concentrated heat source directed to the kidney region of the user's lower back, thereby to provide the user's body with an overall heating effect.

The present invention was developed to overcome these and other drawbacks of the prior devices by providing an adjustable light-weight warming belt adapted to encircle the kidney region of the user's lower back. The belt includes pockets arranged to position heating elements opposite the user's kidneys, thereby to warm the user's kidney's which in turn distribute warmth to the user's entire body.

SUMMARY OF THE INVENTION

Accordingly, it is a primary object of the present invention to provide a flexible, adjustable warming belt adapted to encircle the kidney portion of the user's torso. The belt includes pockets arranged to accurately support body-warming heater means directly opposite the user's kidneys, thereby to efficiently warm the user.

It is a further object of the present invention to provide a warming belt which is simple to construct.

It is another object of the invention to provide a warming belt which is compact and light-weight.

It is yet a further object of the invention to provide a warming belt which uses oxygen-activated chemical heating pouches.

Another object of the present invention is to provide a warming belt having pockets which are longitudinally adjustable on the belt to facilitate placement of the pockets in close proximity with the user's kidneys.

BRIEF DESCRIPTION OF THE DRAWINGS

Other objects and advantages of the invention will become apparent from a study of the following specification when viewed in light of the accompanying drawings, in which:

FIG. 1 is a plan view of the warming belt according to the invention;

FIG. 2 is a sectional view taken along line 2—2 of FIG. 1;

FIG. 3 is a sectional view taken along line 3—3 of FIG. 1;

FIG. 4 is a plan view of a chemical heating pouch;

FIG. 5 is a sectional view taken along line 5—5 of FIG. 4;

FIG. 6 is a plan view of a second embodiment of the invention in which the location of the pockets is adjustable along the length of the belt;

FIG. 7 is a plan view of a detachable pocket for use with the belt of FIG. 6 showing the surface which fastens to the belt;

FIG. 8 is a plan view of the opposite side of the detachable pocket of FIG. 7.

DETAILED DESCRIPTION

Figure 9:
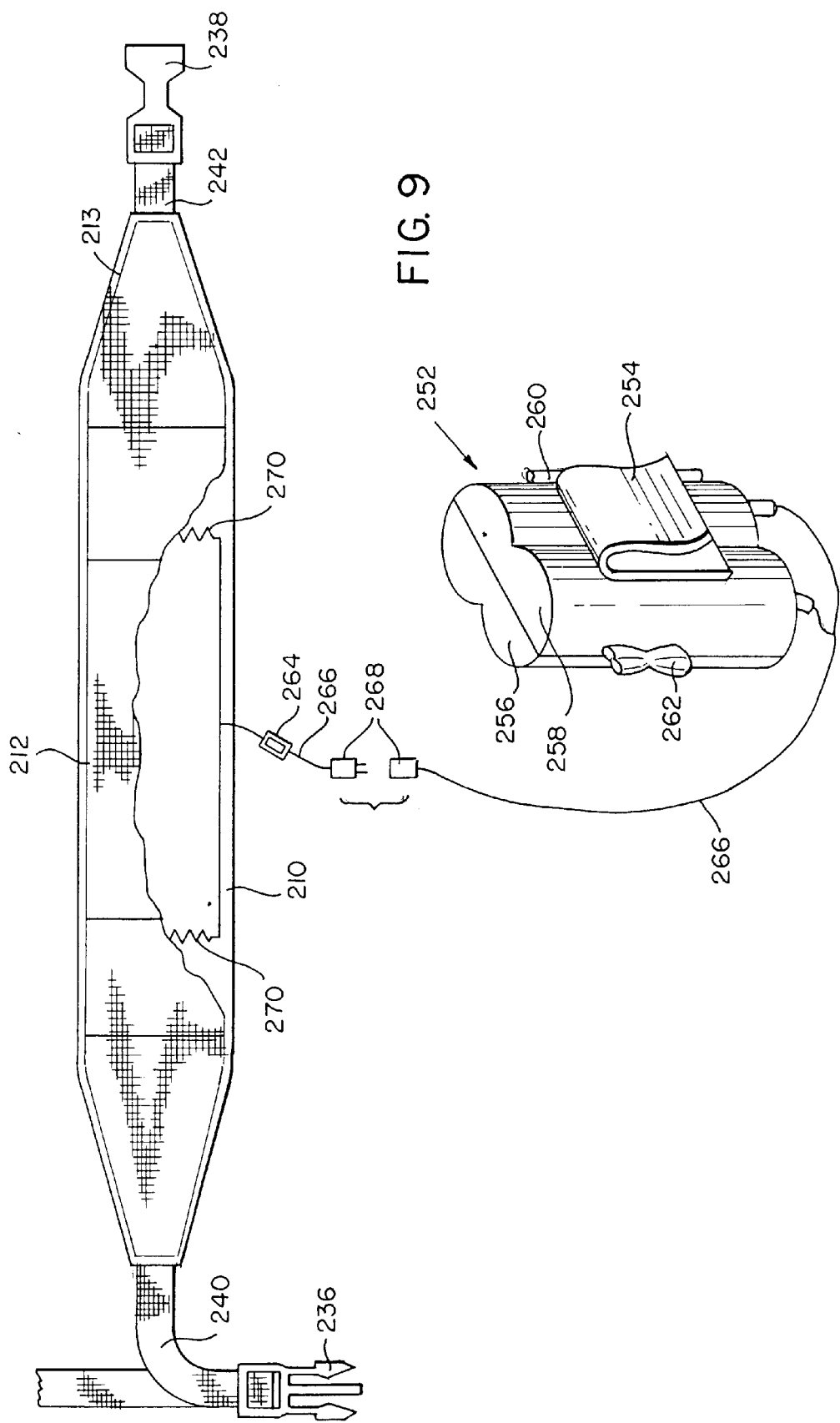
FIG. 9 is a partial cutaway view of a third embodiment of the invention.

Referring first to FIG. 1, there is shown a warming belt 2 including a first tapered end portion 2a, an elongated central body portion 2b having a pair of pockets 6 formed therein adapted to receive heat generating chemical pouches, and a second tapered end portion 2c. As shown in FIGS. 2 and 3, the central body portion is constructed from first 10 and second 12 longitudinally extending layers of fabric which are sewn together along their respective outer edges as indicated by seam line 13 except along two selected intervals 14 along the top edge 16 of the belt. These intervals define access openings 15 (FIG. 2) to the pockets and lie between transverse seams 18, 20, 22, 24 sewn into the belt which define the sides of the pockets. This simple manner of construction, in which the pockets are formed integrally with the belt, requires few steps and wastes little fabric. Closure flaps 26 are sewn to the first fabric layer 10 along the selected intervals along the top edge of the belt as well as along the seams 18, 20, 22, 24 defining the sides of the pockets. The unfastened end 28 of each closure flap extends externally over the second layer 12 in an overlapping fashion thereby acting to retain the chemical heating pouches 30 in their respective pocket. Alternatively, button, snap, zipper or other closure means may be provided. The closure flaps also prevent heat from escaping into the surrounding environment and allow spent heating pouches to be quickly and easily replaced.

One example of a commercially available heating pouch, shown in FIGS. 4 and 5, is the MEDIHEAT product produced by Heatmax, Inc. of Dalton, Ga. The pouch includes a porous cover layer 32 containing an oxygen-activated mixture 34 which includes activated charcoal, iron powder, saltwater and wood fibers. This heating pouch normally has an operating life of about six (6) hours.

In accordance with an important feature of the invention, the pockets have oversized length dimensions $L_1$ relative to the length dimension $L_2$ of the heating pouches, thereby to afford adjustment of the pouches directly opposite the kidney regions of the wearer.

The end portions of the belt 2 include conventional interlocking male 36 and female 38 connectors fastened to straps 40 and 42, respectively. The location of the male connector on strap 40 can be varied to allow the overall length of the belt to be adjusted to fit securely on different sized users. Alternately, other known adjustable belt fastening means could be used as well.

FIGS. 6–8 show a second warming belt embodiment having a pair of detachable pockets 144. The back surface 146 (FIG. 7) of the removable pocket is provided with strips of VELCRO 148 (i.e., hook and loop fasteners) which adhere to corresponding longitudinally extending VELCRO strips 150 provided on the central body portion 104 of the belt. This allows the pockets to be removed and positioned at various locations on the belt directly opposite the wearer's kidneys, thereby to allow one belt to be custom-sized to the individual user. The front of the pocket (FIG. 8) is provided with a closure flap 126 for retaining the chemical heating pouch 130 in the pocket and for providing access thereto, as described previously.

FIG. 9 shows a third embodiment of the invention in which heat is produced by a battery-powered heating unit 270. The heating unit includes a battery pack 252 which houses batteries (not shown). A clip 254 is provided on the pack for mounting the same at various locations on the belt directly opposite the user's kidneys. For quick and easy battery replacement, the pack is constructed from two mating half-shells 256, 258 pivotally connected by a hinge 260. A closure clasp 262 is provided to hold the pack closed. An on/off switch 264 is provided on the power supply line 266 which connects the pack with the belt and includes a connector 268. Heating elements 270 are contained between the first and second layers, 210 and 212, respectively, of the belt. Thus, when the switch is turned on, electrical current flows through the heating elements thereby generating heat which, in turn, is transferred to the two kidney regions of the back of the user.

While in accordance with the provisions of the Patent Statutes the preferred forms and embodiments of the invention have been illustrated and described, it will be apparent to those of ordinary skill in the art that various changes and modifications may be made without deviating from the inventive concept set forth above.

What is claimed is:

1. An adjustable-length body warmer belt adapted for outdoor use by sportsmen and the like for applying heat adjacent the kidneys of the wearer, comprising:
   (a) a fabric body member (2) including an elongated central body portion (2b), and a pair of tapered end portions (2a,2c) each of which progressively converges outwardly from said central body portion;
   (b) means defining a pair of longitudinally-spaced pockets (6) at the remote ends of said elongated central body portion adjacent said tapered end positions, respectively, said pockets having substantially the same longitudinal dimension;
   (c) variable-length connector means for connecting said belt end portions to mount said body member circumferentially around the waist of the wearer with the central body portion adjacent the lower back portion of the wearer, said connector means including:
      (1) a pair of belt straps (40,42) connected with the remote ends of said body member tapered end portions, respectively; and
      (2) adjustable length fastener means (36,38) for connecting said belt straps in accordance with the size of the wearer; and
      (3) each of said pockets having an upper portion containing an access opening (15) that extends longitudinally of said central body portion when the belt is mounted circumferentially around the waist of the wearer; and
   (d) a pair of oxygen-activated chemical heating pouches (30) introduced into said pockets via said access openings, respectively, the longitudinal dimension of each of said heating pouches being less than the corresponding longitudinal dimension of the associated pocket, thereby to permit accurate positioning of said heating pouches opposite the wearer's kidneys, respectively.

2. A body warmer belt as defined in claim 1, and further including:
   (f) a pair of closure means for closing the access openings of said pockets, respectively.

3. A body warmer belt for heating the kidneys of an outdoors sportsman, comprising:
   (a) a fabric body member (2) including an elongated central body portion (2b), and a pair of tapered end portions (2a, 2c) each of which progressively converges in the direction away from said central body portion, said body and end portions consisting of two layers (10,12) of folded fabric material;
   (b) two pairs of transversely extending seams (18, 20; 22, 24) spaced longitudinally of said central body portion for defining a pair of pockets (6) at opposite ends of said central body portion adjacent said tapered end portions, respectively;
   (c) variable-length connector means for connecting said belt end portions to mount said body member circumferentially around the waist of the wearer with the central body portion arranged adjacent the lower back portion of the wearer, said connector means including:
      (1) a pair of belt straps (40, 42) connected with the remote ends of said body member tapered portions, respectively; and
      (2) adjustable length fastener means (36, 38) for connecting said belt straps in accordance with the size of the wearer;
      (3) each of said pockets having an upper portion containing an access opening (15) that extends longitudinally of said central body portion when the belt is mounted circumferentially around the waist of the user; and
   (d) a pair of oxygen-activated chemical heating pouches (30) introduced into said pockets via said access openings, respectively, the longitudinal dimension of each of said heating pouches being less than the corresponding longitudinal dimension of the associated pocket, thereby to permit accurate, positioning of said heating pouches opposite the kidneys of the wearer, respectively.

* * * * *